(12) United States Patent
Shaw

(10) Patent No.: US 8,889,628 B2
(45) Date of Patent: Nov. 18, 2014

(54) SOLUBLE TANDEM SELECTIN GLYCOPROTEIN LIGAND MOLECULES

(71) Applicant: Gray D Shaw, Redwood City, CA (US)

(72) Inventor: Gray D Shaw, Redwood City, CA (US)

( * ) Notice: Subject to any disclaimer, the term of this patent is extended or adjusted under 35 U.S.C. 154(b) by 0 days.

(21) Appl. No.: 13/688,187

(22) Filed: Nov. 28, 2012

(65) Prior Publication Data

US 2013/0136741 A1 May 30, 2013

Related U.S. Application Data

(60) Provisional application No. 61/564,275, filed on Nov. 28, 2011.

(51) Int. Cl.
*C07K 14/705* (2006.01)
*C07K 19/00* (2006.01)

(52) U.S. Cl.
CPC .............. *C07K 14/705* (2013.01); *C07K 19/00* (2013.01); *C07K 14/70564* (2013.01); *C07K 14/70596* (2013.01); *C07K 2319/00* (2013.01); *C07K 2319/02* (2013.01); *C07K 2319/30* (2013.01); *C07K 2319/50* (2013.01)
USPC ..... 514/19.1; 424/134.1; 530/350; 530/387.3

(58) Field of Classification Search
None
See application file for complete search history.

(56) References Cited

U.S. PATENT DOCUMENTS

| | | | |
|---|---|---|---|
| 6,277,975 B1 * | 8/2001 | Larsen et al. | 536/23.4 |
| 2003/0083258 A1 * | 5/2003 | Eppihimer et al. | 514/12 |
| 2003/0138931 A1 * | 7/2003 | Luche et al. | 435/194 |
| 2003/0166521 A1 | 9/2003 | Eppihimer | |
| 2008/0280327 A1 * | 11/2008 | Larsen et al. | 435/69.7 |
| 2009/0117112 A1 * | 5/2009 | Smith et al. | 424/136.1 |

FOREIGN PATENT DOCUMENTS

WO 9808949 3/1998

OTHER PUBLICATIONS

Attwood, Science 290: 471-473, 2000.*
Skolnick et al., Trends in Biotech. 18: 34-39, 2000.*
Ramachandran et al., PNAS 98: 10166-1017, 2001.*
Snapp et al., J. Cell Biology. 142: 263-270, 1998.*
Martinez, JBC, 280:5378-5390 (2005).
Kansas, Blood 88:3259-3287 (1996).
Kumar et al., Blood 88: 3872-3879 (1996).
Somers et al., Cell 103:467-479 (2000).
Somers et al., Cell 105:971 (2001) (erratum for 4 above).
Ramachandran et al., PNAS 96:13771-13776 (1999).
Sako et al., Cell 83:323-331 (1995).

* cited by examiner

*Primary Examiner* — Phillip Gambel
(74) *Attorney, Agent, or Firm* — Steven R. Lazar

(57) ABSTRACT

Recombinant proteins comprised of multiple selectin binding domains derived from the glycopeptide PSGL-1, in a novel tandem configuration, are disclosed, including their fusions with immunoglobulins and/or other polypeptides. Polynucleotides encoding such proteins, compositions and kits containing such proteins, and methods of using such proteins are also disclosed.

12 Claims, 4 Drawing Sheets

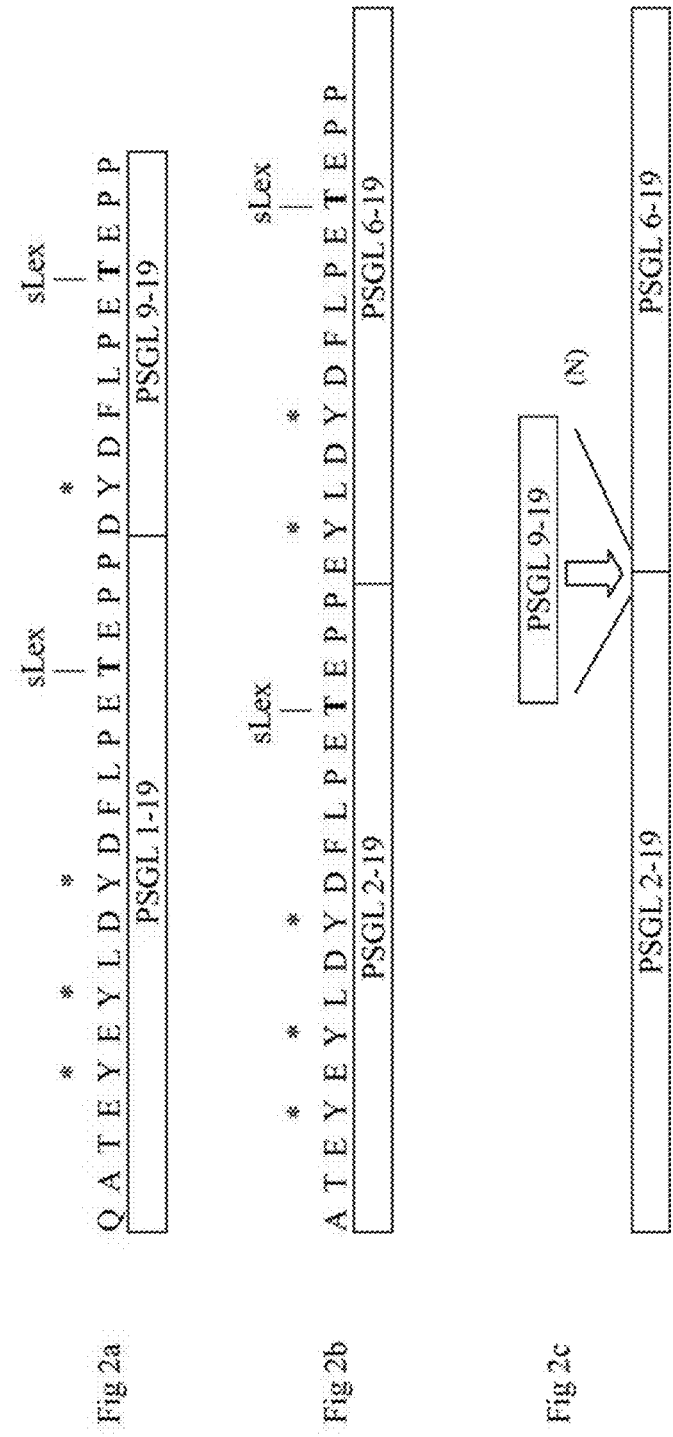

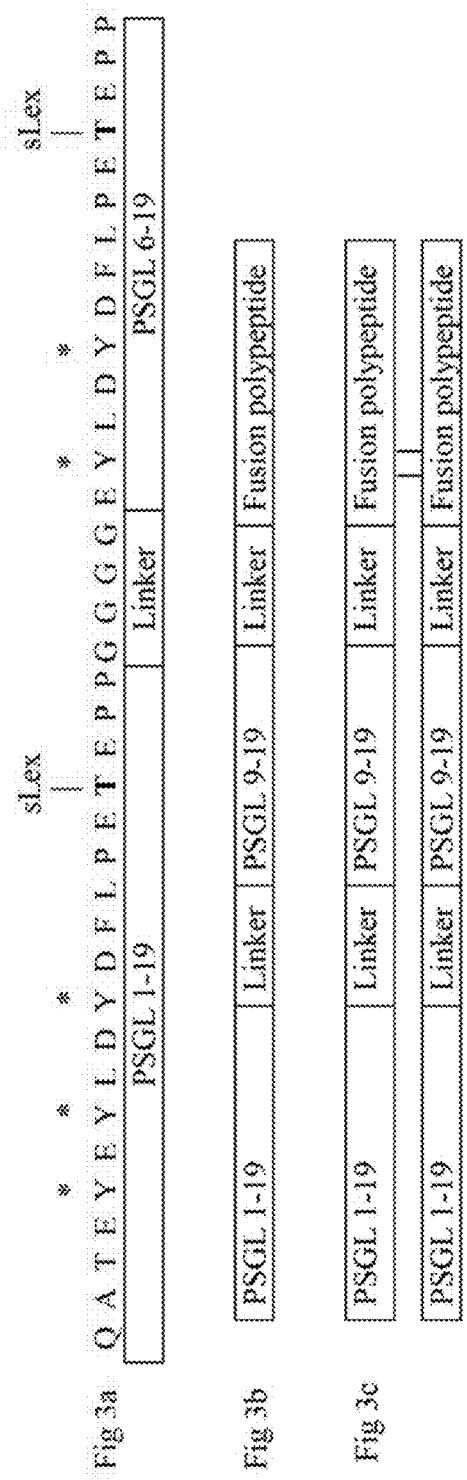

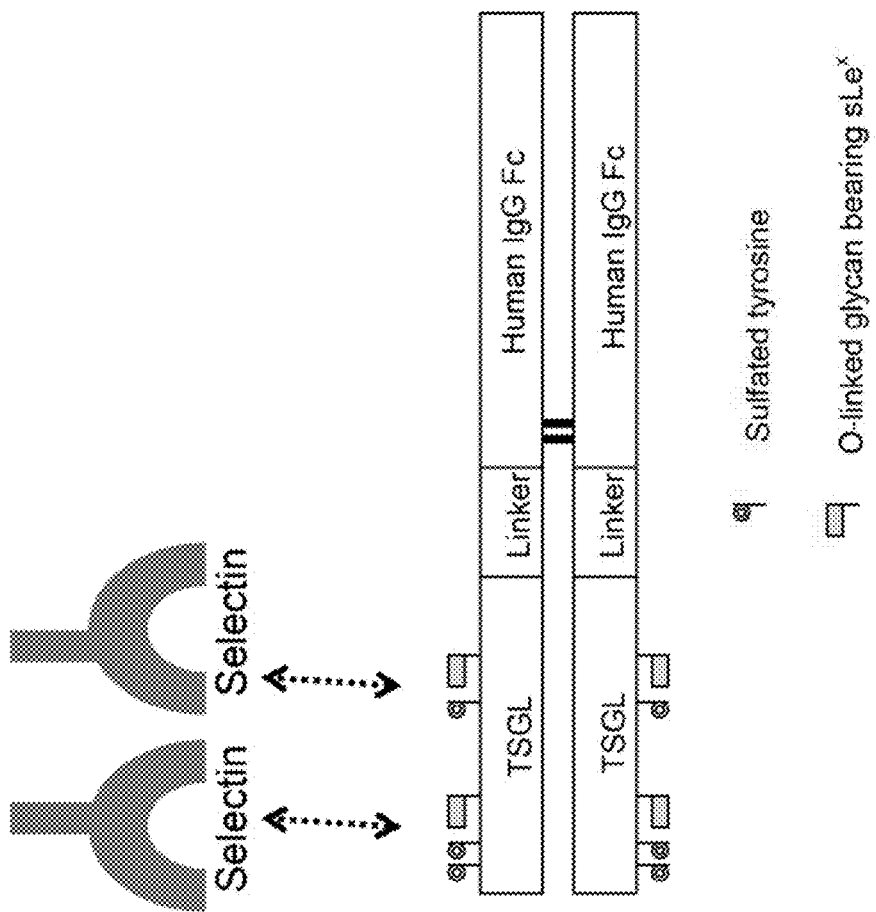

SOLUBLE TANDEM SELECTIN GLYCOPROTEIN LIGAND MOLECULES

RELATED APPLICATION

The present application claims priority from provisional filing 61/561,275, filed, on Nov. 28, 2012, the disclosure, claims and drawings of which are hereby incorporated herein by reference.

TECHNICAL FIELD

The present invention relates to the field of anti-inflammatory and anti-thrombotic substances which act by inhibiting leukocyte adhesion to activated endothelial cells and platelets. More particularly, the present invention is directed to novel, enhanced antagonists of selectin adhesion molecules.

BACKGROUND OF THE INVENTION

The selectins (CD62P, CD62E, CD63L) are a family of C-type lectin cell adhesion molecules expressed, among other places, on certain types of circulating blood cells and on the activated vascular endothelium. During inflammation, leukocytes adhere to the vascular endothelium and enter subendothelial tissue, an interaction that is initially mediated by specific binding of the selectins to ligands on the surface of circulating cells. Such selectin-mediated cellular adhesion occurs during vascular inflammation, thrombotic disorders, parasitic diseases, and may be also implicated in metastatic spread of tumor cells. The selectin proteins are characterized by an N-terminal lectin-like domain, an epidermal growth factor-like domain, and regions of homology to complement binding proteins. Three human selectin proteins have been identified. E-selectin (formerly ELAM-1), L-selectin (formerly LAM-1) and P-selectin (formerly PADGEM or GMP-140), E-selectin is induced on endothelial cells several hours after activation by cytokines, mediating the calcium-dependent interaction between neutrophils and the endothelium. L-selectin is the lymphocyte homing receptor, and P-selectin rapidly appears on the cell surface of platelets when they are activated, mediating calcium-dependent adhesion of neutrophils or monocytes to platelets. P-selectin is also found in the Weibel-Palade bodies of endothelial cells; upon its release from these vesicles P-selectin mediates early binding of neutrophils to histamine- or thrombin-stimulated endothelium. All three of the selectins bind, with varying affinity, to a ligand called PSGL (P-selectin glycoprotein ligand and also known as "PSGL-1"). Interaction of selectins with PSGL, which is expressed on some circulating lymphocytes and leukocytes, causes those circulating cells in the vasculature which express the active form of PSGL to attach to platelets and/or the endothelium where other adhesion molecules and chemokines then mediate extravasatin into the surrounding tissues. Thus, the selectin PSGL interaction has been a well-documented step in the development of inflammatory and immune responses, including vaso-occlusive crisis in sickle cell disease patients.

The cDNA encoding human PSGL (also termed PSGL-1 or SELPLG or CD162) has been cloned and is well-characterized as described in Larsen et al., WO98/08949, and U.S. Pat. No. 6,277,975, the disclosure and claims of which are hereby incorporated herein by reference. The application discloses polynucleotides encoding various forms of recombinant PSGL molecules, including numerous functional soluble forms of PSGL. Thus, PSGL is a well-characterized molecule, soluble forms of which are particularly amenable to administration as therapeutics to block selectin-mediated cell adhesion events (Busuttil et al., Am J Transplant, 11:786-97 (201); Mertens et al., Am Heart J., 152:125 e1-e8(2006)).

The human form of PSGL contains over 300 amino acids in its extracellular domain (See, Uniprot database accession number Q14242). Remarkably, the principal binding site for P and L-selectin exists within a short 19 amino acid segment at the amino terminus of the mature form of PSGL. The highest reported affinity measurements of soluble monomeric forms of PSGL demonstrate $K_D$ values of approximately 200-778 nM when binding to P-selectin (Somers et al., Cell, 103:467-79 (200); Leppanen et al., J. Biol. Chem., 274:24838-48 (1999)). The binding affinity to E-selectin may vary according to the type and number of modified glycans present on the soluble form of PSGL. (Martinez et al., J. Biol. Chem 280:5378-5390 (2005) PSGL-1 interaction with selectins on their respective cell type, including soluble recombinant forms of PSGL-L has been shown to induce signaling via the selectin molecules. The extent to which the selectin molecules are cross linked or clustered on the surface of a cell may dictate the characteristics of such selectin mediated signaling events generated in a particular cell type (Yoshida at el., J Immunol 1998; 161; 933-941). Moreover, it has been demonstrated that the chemokine CCL27 binds to the sulfated tyrosines at the amino terminus of human PSGL-1 (Hirata et al J. Biol. Chem. 279, 51775-51782, 2004). Therefore, with the objective of developing antagonist to selectin-mediated binding events it would be desirable to engineer novel soluble forms of PSGL that have enhanced chemokine and selectin binding properties and are optimized for therapeutic usage.

BRIEF SUMMARY OF THE INVENTION

The present invention describes novel, enhanced soluble selectin ligands that have an increased selectin binding activity as compared with the corresponding soluble form of native human PSGL, as previously described. To create enhanced soluble selectin ligands, a two or more sulfated glycoprotein peptide sequences from PSGL are combined in a tandem configuration on a single polypeptide chain. The second P-selectin ligand site also contain at least one sulfated tyrosine and at least one O-linked glycan having a sialyl Lewis x (sLe$^x$) epitope. These soluble tandem selectin glycoprotein ligands (termed "TSGL" domains) have enhanced selectin binding properties. In preferred embodiments, the TSGL domains are fused with non-TSGL domain polypeptides, such as an immunoglobulin Fc, to form a TSGL fusion protein. Moreover, the described soluble TSGL molecules have suitable biological and pharmacokinetic properties for use as therapeutic agents in humans. Methods are further described for using soluble TSGL molecules to treat humans with graft-vs-host disease, multiple myeloma, or vaso-occlusive, thrombotic or inflammatory disorders.

Accordingly, in one aspect, the invention provides soluble tandem selectin glycoprotein ligand (TSGL) molecules comprising at least two P-selectin glycoprotein ligand (PSGL) domains combined in a tandem configuration along the same polypeptide chain. The PSGL domains of such molecule preferably comprise at least one sulfated tyrosine and at least one O-linked glycan bearing a sialyl Lewis x (sLe$^x$) epitope. The TSGL molecules may be fused to a non-TSGL polypeptide. Suitable non-TSGL polypeptides include, but are not limited to, an immunoglobulin Fc: SolCD39, a Kunitz domain polypeptide, a fibronectin type III domain, an XTEN polypeptide or MAP-1 (Skjoedt et al., J. Bio. Chem. 2010; 285: 8234-8243 and Pavlov et al., Circulation 2012; 126: 2227-2235). In certain preferred embodiments, the TSGL molecule comprises an ammo acid sequence having at least 70%, 80% or 90% sequence identity to the amino acid sequence of SEQ ID NO: 4. More preferably, the TSGL molecule comprises the amino acid sequence of SEQ ID NO: 4, or a functional variant thereof having at least 70% sequence identity to the amino acid sequence of SEQ ID NO: 4.

In another aspect, the present invention provides DNA sequence encoding a soluble tandem selectin glycoprotein ligand (TSGL) molecule comprising at least two P-selectin glycoprotein ligand (PSGL) domains combined in a tandem configuration along the same polypeptide chain. The PSGL domains preferably comprise at least one sulfated tyrosine and an at least one O-linked glycan bearing a sialyl Lewis x (sLe$^x$) epitope. In certain embodiments, the DNA sequence encodes a TSGL molecule fused to a non-TSGL polypeptide. Suitable non-TSGL polypeptides include, but are not limited to, immunoglobulin Fc; SolCD39, a Kunitz domain polypeptide, a fibronectin type II domain, MAP-1, or an XTEN polypeptide. In certain preferred embodiments, the DNA sequence encodes a TSGL molecule comprising an amino acid sequence having at least 70%, 80% or 90% sequence identity to the amino acid sequence of SEQ ID NO: 4. More preferably, the DNA sequence encodes a TSGL molecule comprising the amino acid sequence of SEQ ID NO: 4, or a functional variant thereof having at least 70% sequence identity to the amino acid sequence of SEQ ID NO: 4. In other embodiments, the DNA sequence comprises a nucleotide sequence having at least 60%, 70%, 80%, 9%, 95% sequence identity to the nucleotide sequence of SEQ ID NO: 3. In a particular embodiment, the DNA sequence comprises the nucleotide sequence of SEQ ID NO: 3.

In yet another aspect, the present invention provides methods of treating a disorder in a human subject with a soluble tandem selectin glycoprotein ligand (TSGL) molecule, wherein the disorder is selected from a group consisting of: multiple myeloma (Azab et al., Blood, 119:1468 (2012)), an inflammatory disorder, a thrombotic disorder or a vaso-occlusive disorder, such as is observed in patients with sickle cell anemia. In preferred embodiments, the TSGL molecule comprises an amino acid sequence having at least 70%, 80% or 90% sequence identity to the amino acid sequence of SEQ ID NO: 4. More preferably, the TSGL molecule comprises the amino acid sequence of SEQ ID NO: 4, or a functional variant thereof having at least 70% sequence identity to the amino acid sequence of SEQ ID NO: 4.

BRIEF DESCRIPTION OF THE FIGURES

FIG. 1a illustrates the sequence of the monomeric sulfated PSGL-1 glycopeptide domain [PSGL-19], wherein the designation "[PSGL1-19]" means that the domain comprises amino acids 1 through 19 of the principal binding site for P and L-selectin found within human PSGL-1, illustrated at SEQ ID NO: 2, FIG. 1b illustrates the sequence of the monomeric sulfated PSGL-domain [PSGL4-19]. FIG. 1c illustrates the sequence of the monomeric sulfated PSGL-1 glycopeptide domain [PSGL4-19 [Y5F]], in which the tyrosine at amino acid residue 5 of the principal binding site for P and L-selectin found within human PSGL-1 has been converted to a phenylalanine. FIG. 1d illustrates the sequence of the monomeric sulfated PSGL-1 glycopeptide domain [=PSGL9-19].

FIG. 2 illustrates the protein structure of the tandem configuration of sulfated PSGL-1 glycopeptide domains within the present invention. [TSGLs], FIG. 2a illustrates the structure of TSGL [PSGL1-19:PSGL9-19], wherein the designation "[PSGL1-19:PSGL 9-19]" means that the TSGL comprises a first domain that comprises amino acids 1 through 19 of the principal binding site for P and L-selectin found within human PSGL-1; fused to a second domain that comprises amino acids 9 through 19 of the principal binding site for P and L-selectin found within human PSGL-1 FIG. 2b illustrates the structure of the TSGL [PSGL2-9:PSGL-6-19]. FIG. 2c illustrates the structure of the TSGL [PSGL2-19:(PSGL9-19)$_N$:PSGL6-19] within the present invention that contains more than two sulfated PSGL-1 glycopeptide domains, wherein N is one or greater and represents the number of sulfated PSGL9-19 glycopeptide domains between [PSGL2-19] and [PSGL6-19].

FIG. 3 illustrates the protein structure and configuration of TSGL fusion proteins of the present invention with linker sequences between the two monomeric sulfated PSGL-1 glycopeptide domains of the TSGL and between the TSGL and the fusion polypeptide. FIG. 3a illustrates the amino acid sequence and structure of the TSGL [PSGL1-19:linker:PSGL5-19]. FIG. 3b illustrates the structure of the monomeric TSGL fusion protein [PSGL1-19:linker:PSGL9-19:linker:fusion polypeptide]. The fusion polypeptide may comprise, for example, an Fc region. FIG. 3c illustrates the structure of a multimeric TSGL fusion protein of the present invention. In this case two TSGL fusion proteins are linked via bonds between the two fusion polypeptides. For example, the fusion polypeptide region may each comprise an Fc region, and the two Fc regions may be linked to each other by means of a covalent disulfide bond.

FIG. 4 illustrates the structure and mechanism of enhanced selectin binding exhibited by a TSGL fusion protein of the present invention. In FIG. 4, each monomeric sulfated PSGL-1 glycopeptide domain presents a binding site for selectin, such that multiple selectins are able to bind to the TSGL fusion protein of the present invention.

BRIEF DESCRIPTION OF THE SEQUENCES

Figure 1:
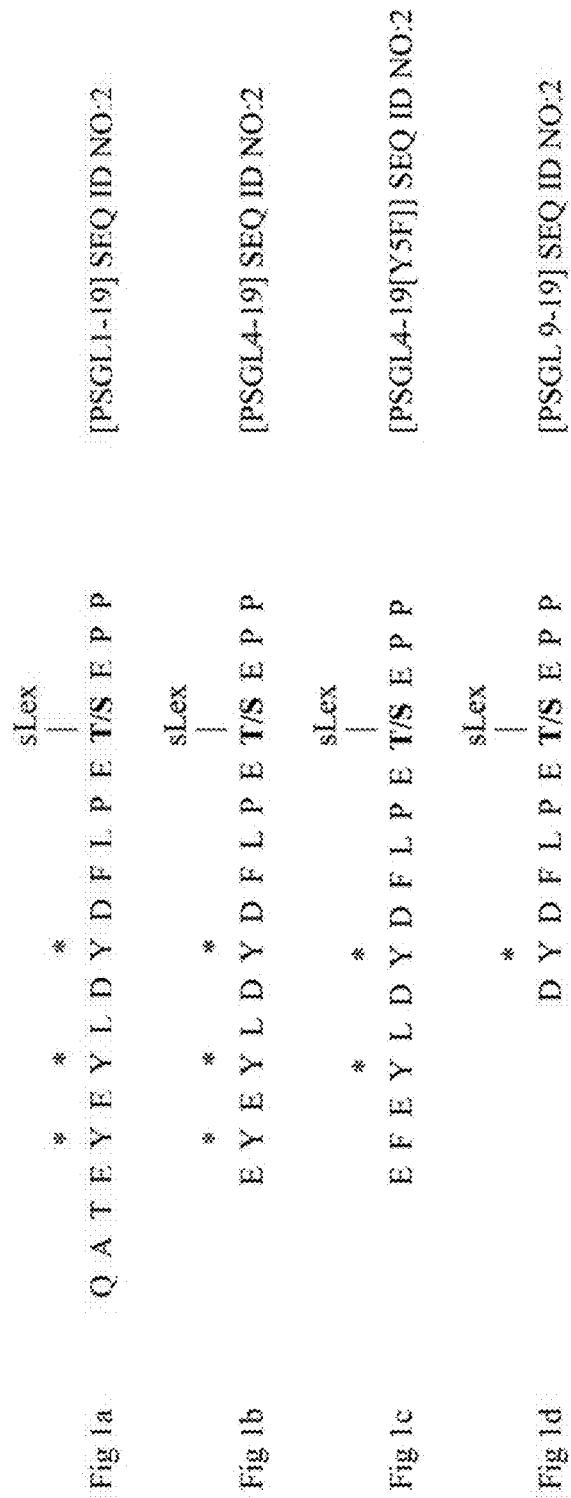
FIG. 1 illustrates the protein structure of various monomeric sulfated PSGL-1 glycopeptide domains within the present invention. In each of the monomeric sulfated PSGL-1 glycopeptide domains, at least one tyrosine residue is sulfated, and the threonine, or serine residue is the site of an 0-linked glycan bearing a sialyl Lewis x (sLex) epitope (illustrated by the letters (T/S)).

SEQ ID NO: 1 is the amino acid sequence of human PSGL-1.

SEQ ID NO: 2 is the amino acid sequence of the principal binding site for P and L-selectin found within human PSGL-1.

SEQ ID NO: 3 is a nucleotide sequence encoding a tandem soluble glycoprotein ligand fusion protein, TSGL[PSGL1-19:PSGL5-19]-Fc, which is a TSGL fusion protein that is illustrative of the present invention.

SEQ ID NO: 4 is the protein sequence encoding a tandem soluble glycoprotein ligand fusion protein, TSGL[PSGL1-19:PSGL5-19]-Fc, which is a TSGL fusion protein that is illustrative of the present invention.

DETAILED DESCRIPTION OF PREFERRED EMBODIMENTS

Human PSGL-1 is 412 amino acid protein (SEQ ID NO: 1) including a 17 amino acid N-terminal signal peptide (amino acids 1-17, a 24 amino acid N-terminal propeptide (amino acids 18-41) and a 371 amino acid P-selectin glycoprotein ligand 1 chain (amino acids 42-412).

SEQ ID NO: 1:
```
MPLQLLLLLI LLGPGNSLQL WDTWADEAEK ALGPLLARDR RQATEYEYLD YDFLPETEPP

EMLRNSTDTT PLTGPGTPES TTVEPAARRS TGLDAGGAVT ELTTELANMG NLSTDSAAME

IQTTQPAATE AQTTQPVPTE AQTTPLAATE AQTTRLTATE AQTTPLAATE AQTTPPAATE

AQTTQPTGLE AQTTAPAAME AQTTAPAAME AQTTPPAAME AQTTQTTAME AQTTAPEATE

AQTTQPTATE AQTTPLAAME ALSTEPSATE ALSMEPTTKR GLFIPFSVSS VTHKGIPMAA

SNLSVNYPVG APDHISVKQC LLAILILALV ATIFFVCTVV LAVRLSRKGH MYPVRNYSPT

EMVCISSLLP DGGEGPSATA NGGLSKAKSP GLTPEPREDR EGDDLTLHSF LP
```

The principal binding site for P and L-selectin is found within a 19 amino acid segment at the amino terminus of the mature form of PSGL from amino acids 42 to 60 (SEQ ID NO: 2).

SEQ ID NO: 2: QATEYEYLDY DFLPETEPP

Soluble forms of TSGL, including fusion proteins comprising enhanced TSGL sequences, can be expressed and purified from mammalian host cells, such as a Chinese hamster ovary cells (CHO) or COS cells. Suitable host cells are capable of attaching carbohydrate side chains characteristic of functional TSGL proteins. Such capability may arise by virtue of the presence of a suitable glycosylating enzyme within the host cell, whether naturally occurring, induced by chemical mutagenesis, or through transfection of the host cell with a suitable expression plasmid containing a DNA sequence encoding the glycosylating enzyme. These host cells can be transfected with expression vectors to enable, via posttranslational modification, the generation of the sialyl Lewis$^x$ epitope on the N-linked and O-linked glycans of enhanced PSGL polypeptides. In the case of CHO-10 cells this requires the co-expression of an α-1,3/1,4 fucosyltranseferase (Kukowska-Latallo et al., Genes Dev. 4:1288-303, 1990) and Core2 β-1,6-N-acetylglucosaminyltransferase enzymes (Kumar et al., Blood 88:3872-79, 1996). The presence of the sialyl Lewis X epitopes on the N-linked and O-linked glycans of enhanced PSGL and/or immunoglobulin polypeptides may enhance the binding to selectins. In order to optimize processing of the mature N-terminus, these host cells may also be transfected with expression vectors with cDNA encoding a form of PACE, also known as furin, is disclosed in van den Ouweland et al., Nucl. Acids Res. 18, 664 (1990), the full disclosure of which is hereby incorporated herein by reference.

The principal binding site contains three tyrosines residues [at amino acids 5, 7 and 10 of SEQ ID NO: 2] for potential sulfation; and one threonine residue [at amino acid residue 16 of SEQ ID NO: 2] for an O-linked glycan bearing a sialyl Lewis x (sLe$^x$) epitope. Accordingly, in a preferred embodiment, each monomeric sulfated PSGL-1 glycopeptide domain contained within the TSGL proteins of the present invention may comprise at least amino acids residues 10 to 16 of SEQ ID NO:2 (YDFLPET). In alternative embodiments, the monomeric sulfated PSGL-1 glycopeptide domain may comprise one or more additional amino acids from the N-terminal end [e.g., amino acids 1-16; 2-16; 3-16; 4-16; 5-16; 6-16; 7-16; 8-16; or 9-16]; one or more additional amino acids from the C-terminal end [e.g., amino acids 10-17; 10-18; 10-19]; or one or more amino additional amino acids from both the N-terminal and C-terminal ends of SEQ ID NO: 2: [e.g. amino acids: 1-17; 2-17; 3-17; 4-17; 5-17; 6-17; 7-17; 8-17; and 9-17; 1-18; 2-18; 3-18; 4-18, 5-18; 6-18; 7-18; 8-18; and 9-18; or 1-19; 3-19; 3-19; 4-19; 5-19; 6-19; 7-19; 8-19; and 9-19]. In certain embodiments, the TSGL proteins of the present invention comprise at least two sulfated PSGL-1 glycopeptide domains. In other embodiments, the TSGL proteins of the present invention may comprise at least one additional monomeric sulfated PSGL-1 glycopeptide domain, that is, the TSGL protein comprises three or more sulfated. PSGL-1 glycopeptide domains. TSGL proteins containing multiple sulfated residues increases the amount of negative (anionic) charge on the protein TSGL proteins containing multiple sulfated residues can be purified from proteins having fewer sulfated residues (hyposulfated TSGL proteins) using methods similar to those described in U.S. Pat. No. 6,933,370.

A TSGL protein of the present invention may be fused to amino acid sequences derived from one or more other proteins (e.g., a fragment of a protein that exhibits a desired activity), forming a TSGL fusion protein, and the TSGL fusion proteins thereby formed constitute another aspect of the present invention. In any fusion protein incorporating a TSGL protein, the amino acid sequence derived from one or more proteins other than P-selectin ligand can be linked to either the C-terminus or N-terminus of the enhanced TSGL sequence, or both. The linkage may be direct (i.e., without an intervening linking sequence not derived from either protein) or through a linking sequence. In certain embodiments of the invention, the TSGL protein and the fusion polypeptide are expressed from a recombinant DNA sequence which encodes both the TSGL protein and the fusion polypeptide, joined either directly or via a DNA sequence encoding a linker sequence.

Suitable linker sequences are known in the art and include glycine-serine polymers (including, for example, (GS)n, (GSGGS)n [SEQ ID NO: 8], (GGGGS)n [SEQ ID NO: 9], and (GGGS)n [SEQ ID NO: 10], where n is an integer of at least one, e.g., one, two, three, or four), glycine-alanine polymers, alanine-serine polymers, and other flexible linkers. Other examples include peptide linkers described in U.S. Pat. No. 5,073,627, the disclosure of which is hereby incorporated by reference.

Any protein or peptide that is desired to be targeted to cells expressing selectin molecules, for example, activated endothelial cells or activated platelets, can be fused with the TSGL in a TSGL fusion protein of the present invention. Proteins or polypeptides to which the TSGL proteins can be linked include, but are not limited to, SolCD39, Drosopoulos et al., Thromb, Haemost., 103:426-434 (2010), a Kunitz domain polypeptide (see, for example, Dennis and Lazarus. J. Biol. Chem., 269:22137-44 (1994); Nixon and Wood, Current Opinion in Drug Discovery and Development, 9:261-68 (2006)), a fibronectin type III domain (see for example, Dean et al., PNAS USA, 84:1876-80 (1987); Skorstengaard et al., Eur. J. Biochem, 161:441-53 (986), MAP-1 (Skjoedt et al., *J. Biol. Chem.* 2010; 285: 8234-8243 and Pavlov et al., *Circulation* 2012; 126:2227-2235) and XTEN polypeptides (Schellenberger et al, Nat, Biotechnol., 27:1186-90 (2009)). Other proteins or peptides which may be fused to a TSGL to form a TSGL fusion protein of the invention include, but are not limited to, cytokines, such as interleukin-1 receptor antagonist (IL-1Ra; Uniprot accession number P18510), bone morphogenetic proteins (BMPs; for example, BMP-2, Uniprot accession number P12643; BMP-4 Uniprot accession number P12644; BMP-7, Uniprot accession number P18075) and interleukin-11 (IL-11; Uniprot accession number P20809). In other embodiments, the protein or peptide which may be fused to a TSGL to form a TSGL fusion protein of the invention may be an enzyme, for example, including, but are not limited to, SolCD39 (Drosopoulos et al., Thromb. Haemost., 103:426-434 (2010)).

Compositions and Formulations:

In certain embodiments, the composition further comprises one or more surfactants. Exemplary surfactants include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer) carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 118, cetrimonium bromide, cetylpyridinium chloride, benzalkonium chloride, docusate sodium, etc. and/or combinations thereof. In certain embodiments, the surfactant is a Tween surfactant (e.g., Tween 60, Tween 80, etc.).

In certain embodiments, the composition further comprises one or more preservatives. Exemplary preservatives may include antioxidants, chelating agents, antimicrobial preservatives, antifungal preservatives, alcohol preservatives, acidic preservatives, and other preservatives.

In certain embodiments, the one or more preservative comprises an antioxidant. Exemplary antioxidants include, but are not limited to, phosphites, dibutyl phosphite, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, cysteine hydrochloride, thioglycerol, sodium mercaptoacetate, sodium formaldehyde sulfoxylate (SFS), lecithin, and alpha-tocopherol. In certain embodiments, the antioxidant is dibutyl phosphite or sodium bisulfite ($NaHSO_3$).

In certain embodiments, the one or more preservative comprises a chelating agent. Exemplary chelating agents include, but are not limited to, ethytlenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

In certain embodiments, the one or more preservative comprises an antimicrobial preservative. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the one or more preservative comprises an antifungal preservative. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

In certain embodiments, the one or more preservative comprises a alcohol preservative. Exemplary alcohol preservatives include, but are not limited to, ethanol, polyethylene glycol, phenol, phenolic compounds, bisphenol, chlorobutanol, hydroxybenzoate, and phenylethyl alcohol.

In certain embodiments, the one or more preservative comprises an acidic preservative. Exemplary acidic preservatives include, but are not limited to vitamin A, vitamin C, viltamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

In certain embodiments, the composition further comprises one or more diluents. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In certain embodiments, the composition further comprises one or more granulating and/or dispersing agents. Exemplary granulating and/or dispersing agents include, but are not limited to, potato starch, corn starch, tapioca starch, sodium starch glycolate, clays alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfite, quaternary ammonium compounds, etc., and combinations thereof.

In certain embodiments, the composition further comprises one or more binding agents. Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates polyethylene oxide; polyethylene glycol; inorganic calcium salts; silicic acid; polymethacrylates; waxes; water; alcohol; etc.; and combinations thereof.

In certain embodiments, the composition further comprises one or more buffering agents. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-five water, isotonic saline, Ringer's solution, ethyl alcohol, etc., and combinations thereof.

In certain embodiments, the composition further comprises one or more lubricating agents. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

In certain embodiments, the composition further comprises one or more solubilizing or suspending agents. Exemplary solubilizing or suspending agents include, but are not limited to, water, organic solvents, oils, and mixtures thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof. In certain embodiments, the oil is mineral oil.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

The formulations of the pharmaceutical compositions described herein may be prepared by any method known or hereafter developed in the art of pharmacology. In general, such preparatory methods include the step of bringing the active ingredient (i.e. a glycosylated deltorphin variant) into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the active ingredient.

Preferred dosage forms include oral and parenteral dosage forms. Liquid dosage forms for oral and parenteral administration include, but are not limited to pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Compositions for oral administration are typically liquid or in solid dosage forms. Compositions for oral administration may include protease inhibitors, including organic acids such as citric acid, in order to inhibit pancreatic and brush border proteases. Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. No. 5,912,014, U.S. Pat. No. 6,086,918 and U.S. Pat. No. 6,673,574. The disclosure of each of these documents is hereby incorporated herein by reference.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below (65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% 1(w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, comprise 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

The skilled clinician will be able to determine the appropriate dosage amount and number of doses of an agent to be administered to subject, dependent upon both the age and weight of the subject, the underlying condition, and the response of an individual patient to the treatment. In addition, the clinician will be able to determine the appropriate timing for delivery of the agent in a manner effective to treat the subject.

Preferably, the agent is delivered within 48 hours prior to exposure of the patient to an amount of a thrombosis or thrombocytopenia provoking stimulus effective to induce thrombosis or thrombocytopenia, and more preferably, within 36 hours, and more preferably within 24 hours, and more preferably within 12 hours, and more preferably within 6 hours, 5 hours, 4 hours, 3 hours, 2 hours, or 1 hour prior to exposure of the patient to an amount of thrombosis or thrombocytopenia provoking stimulus effective to induce thrombosis or thrombocytopenia, in one embodiment, the agent is administered as soon as it is recognized (i.e., immediately) by the subject or clinician that the subject has been exposed or is about to be exposed to a thrombosis or thrombocytopenia provoking stimulus, and especially a thrombosis or thrombocytopenia provoking stimulus to which the subject is sensitized. In another embodiment, the agent is administered upon the first sign of development of thrombosis or thrombocytopenia, and preferably, within at least 2 hours of the development of symptoms of thrombosis or thrombocytopenia, and more preferably, within at least 1 hour, and more preferably within at least 30 minutes, and more preferably within at least 10 minutes, and more preferably within at least 5 minutes of development of symptoms of thrombosis or thrombocytopenia. Symptoms of thrombosis or thrombocytopenia and methods for measuring or detecting such symptoms have been described and are well known in the art. Preferably, such administrations are given until signs of reduction of thrombosis or thrombocytopenia appear, and then as needed until the symptoms of thrombosis or thrombocytopenia are gone.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the invention are kits that comprise one or more inventive complexes and/or compositions. Kits are typically provided in a suitable container (e.g., for example, a glass, foil, plastic, or cardboard package). In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

Methods of Treatment:

The compositions and kits of the present invention may be useful in treating conditions characterized by P-, E- or L-selectin mediated intercellular adhesion. Such conditions include, without limitation, myocardial infarction bacterial or viral infection, metastatic conditions, inflammatory disorders such as arthritis, gout, uveitis, acute respiratory distress syndrome, asthma, emphysema, delayed type hypersensitivity reaction systemic lupus erythematosus, thermal injury such as burns or frostbite, autoimmune thyroiditis, experimental allergic encephalomyelitis, multiple sclerosis, multiple organ injury syndrome secondary to trauma, diabetes, Reynaud's syndrome, neutrophilic dermatosis (Sweet's syndrome), inflammatory bowel disease, Grave's disease, glomerulonephritis, gingivitis, periodontitis, hemolytic uremic syndrome, ulcerative colitis, Crohn's disease, necrotizing enterocolitis, granulocyte transfusion associated syndrome, cytokine-induced toxicity, and the like.

The compositions and kits of the present invention may also be useful in organ transplantation, both to prepare organs for transplantation and to quell organ transplant rejection, as well as treating graft-vs-host disease. Accordingly, the compositions and kits of the present invention may be administered to a living or non-living organ donor, prior to organ removal, or may be administered "ex-vivo" to the donor organ concomitantly with organ preservation solution, prior to, and/or subsequent to surgical anastomosis with the recipient. The compositions and kits of the present invention may be used to treat hemodialysis and leukophoresis patients. Additionally, the compositions and kits of the present invention may be used as an antimetastatic agent, for example in the treatment of multiple myeloma. The compositions and kits of the present invention may be used itself as an inhibitor of P-, E- or L-selectin-mediated intercellular adhesion or to design inhibitors of selectin-mediated intercellular adhesion. The present invention encompasses both pharmaceutical compositions and kits of the present invention and therapeutic methods of treatment or use that employ the compositions and kits of the present invention.

Additional uses of the compositions and kits of the present invention include treatment of ischemia and reperfusion, bacterial sepsis and disseminated intravascular coagulation, adult respiratory distress syndrome and related pulmonary disorders, tumor metastasis, rheumatoid arthritis and atherosclerosis. Reperfusion injury is a major problem in clinical cardiology. Therapeutic agents that reduce leukocyte adherence in ischemic myocardium can significantly enhance therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., Circulation 67: 1016-1023, 1983). These adherent leukocytes can migrate through the endothelium and destroy ischemic myocardium just as it is being rescued by restoration of blood flow.

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products. Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. Specifically, certain carcinoma cells have been demonstrated to bind to both E-selectin, as reported by Rice and Bevilacqua. Science 246:1303-1306 (1991), and P-selectin, as reported by Aruffo, et al., Proc. Natl. Acad. Sci. USA 89:2292-2296 (1992). The association of platelets with metastasizing tumor cells has been well described, suggestion a role for platelets in the spread of some cancers. Since P-selectin is expressed on activated platelets, it is believed to be involved in association of platelets with at least some malignant tumors.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis. In these clinical applications, the TSGL, or fragments thereof, can be administered to block selectin-dependent interactions by binding competitively to P-selectin expressed on activated cells. In particular, components of the TSGL, which play a key role in recognition by P-selectin, can be administered. Similarly, natural or synthetic analogs of the TSGL or its fragments which bind to P-selectin can also be administered. TSGLs, or fragments thereof, in an appropriate pharmaceutical carrier, are preferably administered intravenously where immediate relief is required. The TSGLs, compositions or fragments thereof can also be administered intramuscularly, intraperitoneally, subcutaneously, orally, as the TSGL, conjugated to a carrier molecule, or in a drag delivery device. TSGLs can be modified chemically to increase its in vivo half-life. See U.S. Pat. No. 6,506,382 and U.S. Pat. No. 8,232,252, the complete disclosures of which are hereby incorporated herein by reference.

Practice of the invention is illustrated in the following, non-limiting examples. The skilled artisan will recognize that many modifications, variations and extensions are possible while remaining within the teachings of the present specification and embodied within the claims.

EXAMPLE 1

TSGL Fusion Proteins

A TSGL with a novel amino acid sequence can be constructed in accordance with the following procedure:

TSGL[PSGL1-19:PSGL6-19]-Fc: A cDNA was constructed encoding the signal peptide, a PACE cleavage site and a 33 amino acid sulfated TSGL sequence fused to a mutated Fc region of human IgG1 at His224 (Kabat et al.) of the native Fc sequence. O-linked glycans bearing the sialyl Lewis x (sLe$^x$) epitope occur at the Thr16 and Thr30 residues of the mature protein.

The sequence of the cDNA construct is reported as SEQ ID NO:3. The amino acid sequence encoded by the cDNA construct is reported as SEQ ID NO:4. The mature amino acid sequence of the encoded fusion protein begins a amino acid 42 of SEQ ID NO:4. The mutations in the Fc portion were a change of Leu 234 and Gly237 of the native Fc sequence to Ala.

```
                                                               SEQ ID NO: 3
atgcctctgcaactcctcctgttgctgatcctactgggccctggcaacagcttgcagctg        60
tgggacacctgggcagatgaagccgagaaagccttgggtcccctgcttgcccgggaccgg
agacaggccaccgaatatgagtacctagattatgatttcctgccagaaacggagcctcca       180
gagtacctagattatgatttcctgccagaaacggagcctccacacacatgcccaccgtgc
ccagcacctgaagccctgggggcaccgtcagtcttcctcttccccccaaaacccaaggac       300
accctcatgatctcccggacccctgaggtcacatgcgtggtggtggacgtgagccacgaa
gaccctgaggtcaagttcaactggtacgtggacggcgtggaggtgcataatgccaagaca       420
aagccgcgggaggagcagtacaacagcacgtaccgtgtggtcagcgtcctcaccgtcctg
caccaggactggctgaatggcaaggagtacaagtgcaaggtctccaacaaagccctccca       540
gcccccatcgagaaaaccatctccaaagccaaagggcagccccgagaaccacaggtgtac
accctgcccccatcccgggatgagctgaccaagaaccaggtcagcctgacctgcctggtc       660
aaaggcttctatcccagcgacatcgccgtggagtgggagagcaatgggcagccggagaac
aactacaagaccacgcctcccgtgctggactccgacggctccttcttcctctacagcaag       780
ctcaccgtggacaagagcaggtggcagcaggggaacgtcttctcatgctccgtgatgcat
gaggctctgcacaaccactacacgcagaagagcctctccctgtctccgggtaaatga     897
                                                               SEQ ID NO: 4
MPLQLLLLLI LLGPGNSLQL WDTWADEAEK ALGPLLARDR RQATEYEYLD YDFLPETEPP

EYLDYDFLPE TEPPHTCPPC PAPEALGAPS VFLFPPKPKD TLMISRTPEV TCVVVDVSHE

DPEVKFNWYV DGVEVHNAKT KPREEQYNST YRVVSVLTVL HQDWLNGKEY KCKVSNKALP

APIEKTISKA KGQPREPQVY TLPPSRDELT KNQVSLTCLV KGFYPSDIAV EWESNGQPEN

NYKTTPPVLD SDGSFFLYSK LTVDKSRWQQ GNVFSCSVMH EALHNHYTQK SLSLSFGK
```

All patents, patent applications and scientific literature references cited in the disclosure are hereby incorporated herein for the cited teachings, as if fully set forth.

---

What is claimed is:

1. A soluble tandem selectin glycoprotein ligand (TSGL) molecule comprising at least two sulfated P-selectin glycoprotein ligand-1 (PSGL-1) domains combined in a tandem configuration along the same polypeptide chain, wherein each of the PSGL-1 domains comprises amino acids 10 to 16 of SEQ ID NO: 2.

2. The TSGL molecule of claim 1 fused to a non-TSGL polypeptide.

3. The TSGL molecule of claim 1 fused to a non-TSGL polypeptide, wherein the non-TSGL polypeptide is an immunoglobulin Fc.

4. The TSGL molecule of claim 1, wherein each of the PSGL-1 domains comprises one or more additional amino acids.

5. A soluble tandem selectin glycoprotein ligand (TSGL) immunoglobulin Fc fusion molecule comprising at least two P-selectin glycoprotein ligand-1 (PSGL-1) domains combined in a tandem configuration along the same polypeptide chain, wherein each of the PSGL-1 domains comprises amino acids 10 to 16 of SEQ ID NO: 2.

6. The TSGL immunoglobulin Fc fusion molecule of claim 5, wherein each of the PSGL-1 domains comprises one or more additional amino acids.

7. The TSGL molecule of claim 1, wherein each of the PSGL-1 domains comprises amino acids 9 to 19 of SEQ ID NO:2.

8. The TSGL molecule of claim 1, wherein each of the PSGL-1 domains comprises amino acids 6 to 19 of SEQ ID NO:2.

9. The TSGL molecule of claim 1, wherein each of the PSGL-1 domains comprises the amino acid sequence of SEQ ID NO: 2.

10. The TSGL immunoglobulin Fc fusion molecule of claim 5, wherein each of the PSGL-1 domains comprises amino acids 10 to 16 of SEQ ID NO: 2.

11. The TSGL immunoglobulin Fc fusion molecule of claim 5, wherein each of the PSGL-1 domains comprises the amino acid sequence of SEQ ID NO: 2.

12. The TSGL immunoglobulin Fc fusion molecule of claim 5, comprising (1) a first PSGL-1 domain comprising the amino acid sequence of SEQ ID NO: 2; (2) a first linker sequence; (3) a second PSGL-1 domain comprising amino acids 9 to 19 of SEQ ID NO: 2; (4) a second linker sequence; and (5) an immunoglobulin Fc fragment.

* * * * *

```
                          SEQUENCE LISTING

<160> NUMBER OF SEQ ID NOS: 10

<210> SEQ ID NO 1
<211> LENGTH: 412
<212> TYPE: PRT
<213> ORGANISM: Homo Sapiens

<400> SEQUENCE: 1

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
            35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Ser Thr Gly Leu Asp Ala Gly
                85                  90                  95
```

```
Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
        115                 120                 125

Thr Glu Ala Gln Thr Thr Gln Pro Val Pro Thr Glu Ala Gln Thr Thr
        130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
                165                 170                 175

Ala Ala Thr Glu Ala Gln Thr Thr Gln Pro Thr Gly Leu Glu Ala Gln
            180                 185                 190

Thr Thr Ala Pro Ala Ala Met Glu Ala Gln Thr Thr Ala Pro Ala Ala
        195                 200                 205

Met Glu Ala Gln Thr Thr Pro Pro Ala Ala Met Glu Ala Gln Thr Thr
        210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
                245                 250                 255

Ala Ala Met Glu Ala Leu Ser Thr Glu Pro Ser Ala Thr Glu Ala Leu
            260                 265                 270

Ser Met Glu Pro Thr Thr Lys Arg Gly Leu Phe Ile Pro Phe Ser Val
        275                 280                 285

Ser Ser Val Thr His Lys Gly Ile Pro Met Ala Ala Ser Asn Leu Ser
        290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
                325                 330                 335

Cys Thr Val Val Leu Ala Val Arg Leu Ser Arg Lys Gly His Met Tyr
            340                 345                 350

Pro Val Arg Asn Tyr Ser Pro Thr Glu Met Val Cys Ile Ser Ser Leu
        355                 360                 365

Leu Pro Asp Gly Gly Glu Gly Pro Ser Ala Thr Ala Asn Gly Gly Leu
        370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
                405                 410

<210> SEQ ID NO 2
<211> LENGTH: 19
<212> TYPE: PRT
<213> ORGANISM: Homo Sapiens
<220> FEATURE:
<221> NAME/KEY: MISC_FEATURE
<222> LOCATION: (16)..(16)
<223> OTHER INFORMATION: Xaa is Thr or Ser

<400> SEQUENCE: 2

Gln Ala Thr Glu Tyr Glu Tyr Leu Asp Tyr Asp Phe Leu Pro Glu Xaa
1               5                   10                  15

Glu Pro Pro

<210> SEQ ID NO 3
```

<211> LENGTH: 897
<212> TYPE: DNA
<213> ORGANISM: Artificial Sequence
<220> FEATURE:
<223> OTHER INFORMATION: DNA encoding Fusion Protein

<400> SEQUENCE: 3

```
atgcctctgc aactcctcct gttgctgatc ctactgggcc ctggcaacag cttgcagctg     60
tgggacacct gggcagatga agccgagaaa gccttgggtc ccctgcttgc ccggaccgg    120
agacaggcca ccgaatatga gtacctagat tatgatttcc tgccagaaac ggagcctcca   180
gagtacctag attatgattt cctgccagaa acggagcctc acacacatg cccaccgtgc    240
ccagcacctg aagccctggg ggcaccgtca gtcttcctct tccccccaaa acccaaggac   300
accctcatga tctcccggac ccctgaggtc acatgcgtgg tggtggacgt gagccacgaa   360
gaccctgagg tcaagttcaa ctggtacgtg gacggcgtgg aggtgcataa tgccaagaca   420
aagccgcggg aggagcagta caacagcacg taccgtgtgg tcagcgtcct caccgtcctg   480
caccaggact ggctgaatgg caaggagtac aagtgcaagg tctccaacaa agccctccca   540
gcccccatcg agaaaaccat ctccaaagcc aagggcagc cccgagaacc acaggtgtac    600
accctgcccc catcccggga tgagctgacc aagaaccagg tcagcctgac ctgcctggtc   660
aaaggcttct atcccagcga catcgccgtg gagtgggaga gcaatgggca gccggagaac   720
aactacaaga ccacgcctcc cgtgctggac tccgacggct ccttcttcct ctacagcaag   780
ctcaccgtgg acaagagcag gtggcagcag gggaacgtct tctcatgctc cgtgatgcat   840
gaggctctgc acaaccacta cacgcagaag agcctctccc tgtctccggg taaatga      897
```

<210> SEQ ID NO 4
<211> LENGTH: 298
<212> TYPE: PRT
<213> ORGANISM: Artificial Sequence
<220> FEATURE:
<223> OTHER INFORMATION: Fusion Protein

<400> SEQUENCE: 4

```
Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
                20                  25                  30

Gly Pro Leu Leu Ala Arg Asp Arg Gln Ala Thr Glu Tyr Glu Tyr
            35                  40                  45

Leu Asp Tyr Asp Phe Leu Pro Glu Thr Glu Pro Pro Glu Tyr Leu Asp
    50                  55                  60

Tyr Asp Phe Leu Pro Glu Thr Glu Pro Pro His Thr Cys Pro Pro Cys
65                  70                  75                  80

Pro Ala Pro Glu Ala Leu Gly Ala Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
```

```
                    165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Asp Glu
        195                 200                 205

Leu Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 5
<211> LENGTH: 16
<212> TYPE: PRT
<213> ORGANISM: Artificial Sequence
<220> FEATURE:
<223> OTHER INFORMATION: PSGL Sulfated Glycopeptide

<400> SEQUENCE: 5

Glu Tyr Glu Tyr Leu Asp Tyr Asp Phe Leu Pro Glu Thr Glu Pro Pro
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: PSGL Sulfated Glycopeptide

<400> SEQUENCE: 6

Glu Phe Glu Tyr Leu Asp Tyr Asp Phe Leu Pro Glu Thr Glu Pro Pro
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: PSGL Sulfated Glycopeptide

<400> SEQUENCE: 7

Asp Tyr Asp Phe Leu Pro Glu Thr Glu Pro Pro
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Linker Peptide

<400> SEQUENCE: 8

Gly Ser Gly Gly Ser
1               5
```

```
<210> SEQ ID NO 9
<211> LENGTH: 5
<212> TYPE: PRT
<213> ORGANISM: Artificial Sequence
<220> FEATURE:
<223> OTHER INFORMATION: Linker Peptide

<400> SEQUENCE: 9

Gly Gly Gly Gly Ser
1               5

<210> SEQ ID NO 10
<211> LENGTH: 4
<212> TYPE: PRT
<213> ORGANISM: Artificial Sequence
<220> FEATURE:
<223> OTHER INFORMATION: Linker Peptide

<400> SEQUENCE: 10

Gly Gly Gly Ser
1
```